(12) United States Patent
Dean

(10) Patent No.: US 7,972,360 B2
(45) Date of Patent: Jul. 5, 2011

(54) METHOD FOR USE IN REPAIRS OF INJURED SOFT TISSUE

(76) Inventor: John C. Dean, Midland, TX (US)

( * ) Notice: Subject to any disclaimer, the term of this patent is extended or adjusted under 35 U.S.C. 154(b) by 928 days.

(21) Appl. No.: 11/866,220

(22) Filed: Oct. 2, 2007

(65) Prior Publication Data

US 2008/0058867 A1 Mar. 6, 2008

Related U.S. Application Data

(62) Division of application No. 10/358,616, filed on Feb. 5, 2003, now Pat. No. 7,303,577.

(51) Int. Cl.
*A61B 17/08* (2006.01)

(52) U.S. Cl. .................................. 606/215; 606/151

(58) Field of Classification Search .................. 606/213, 606/215–217, 219, 220, 232, 233, 300, 151; 623/13.14, 13.15, 13.17, 13.19
See application file for complete search history.

(56) References Cited

U.S. PATENT DOCUMENTS

| 3,166,072 | A | | 1/1965 | Sullivan, Jr. |
| 3,545,008 | A | * | 12/1970 | Bader, Jr ..................... 623/13.15 |
| 3,646,615 | A | | 3/1972 | Ness |
| 4,060,089 | A | | 11/1977 | Noiles |
| 4,548,202 | A | | 10/1985 | Duncan |
| 4,610,250 | A | | 9/1986 | Green |
| 4,776,851 | A | | 10/1988 | Bruchman et al. |
| 4,923,471 | A | | 5/1990 | Morgan |
| 4,943,292 | A | | 7/1990 | Foux |
| 4,960,420 | A | | 10/1990 | Goble et al. |
| 4,988,351 | A | | 1/1991 | Paulos et al. |
| 5,013,316 | A | | 5/1991 | Goble et al. |
| 5,167,665 | A | | 12/1992 | McKinney |
| 5,250,058 | A | | 10/1993 | Miller et al. |
| 5,306,290 | A | | 4/1994 | Martins et al. |
| 5,336,233 | A | | 8/1994 | Chen |
| 5,370,661 | A | | 12/1994 | Branch |
| 5,380,334 | A | | 1/1995 | Torrie et al. |
| D368,777 | S | | 4/1996 | Goble et al. |
| D374,286 | S | | 10/1996 | Goble et al. |
| D374,287 | S | | 10/1996 | Goble et al. |
| 5,601,558 | A | | 2/1997 | Torrie et al. |
| 5,634,926 | A | | 6/1997 | Jobe |

(Continued)

OTHER PUBLICATIONS

Arthrex, "TissueButton(TM)," obtained from http://www.arthrex.com, generated Feb. 9, 2010.

(Continued)

*Primary Examiner* — Julian W Woo
(74) *Attorney, Agent, or Firm* — Wong, Cabello, Lutsch, Rutherford & Brucculeri LLP.

(57) ABSTRACT

A method, system and apparatus for augmenting the surgical repair of soft tissue injuries, in which a first end of a bridge member attaches to a first portion of healthy tissue, and a second end of the bridge member attaches to a second portion of healthy tissue. The bridge member (or bridge members) used to augment the soft tissue repair may be interconnected or function independently. Flexibility and elasticity of the bridge member are determined by the situation and may be altered to improve healing. The device may be used in arthroscopic procedures, and may be manufactured in a variety of lengths, or may be manufactured one length and be cut to the desired length, or otherwise altered to provide an optimal length of the bridge member.

27 Claims, 8 Drawing Sheets

U.S. PATENT DOCUMENTS

| | | | |
|---|---|---|---|
| 5,823,994 | A | 10/1998 | Sharkey et al. |
| D404,128 | S | 1/1999 | Huebner |
| 5,893,856 | A | 4/1999 | Jacob et al. |
| 5,947,999 | A | 9/1999 | Groiso |
| 5,951,590 | A | 9/1999 | Goldfarb |
| 6,027,523 | A | 2/2000 | Schmieding |
| 6,030,410 | A | 2/2000 | Zurbrügg |
| 6,036,704 | A | 3/2000 | Yoon |
| 6,074,409 | A | 6/2000 | Goldfarb |
| 6,093,201 | A | 7/2000 | Cooper et al. |
| 6,096,060 | A | 8/2000 | Fitts et al. |
| 6,117,139 | A * | 9/2000 | Shino .................. 606/300 |
| 6,123,709 | A | 9/2000 | Jones |
| 6,149,669 | A | 11/2000 | Li |
| 6,206,886 | B1 | 3/2001 | Bennett |
| 6,273,903 | B1 | 8/2001 | Wilk |
| 6,726,688 | B2 | 4/2004 | Lerch |
| 7,172,615 | B2 * | 2/2007 | Morriss et al. .......... 606/215 |
| 7,442,202 | B2 | 10/2008 | Dreyfus |

OTHER PUBLICATIONS

Craft, D.V. et al., "Fixation Strength of Rotator Cuff Repairs With Suture Anchors and the Transosseous suture Technique." Journal of Shoulder Elbow Surgery, vol. 5, No. 1 (Jan./Feb. 1996), pp. 32-40.

Rossouw, D.J., et al., "A biomechanical Evaluation of Suture Anchors in Repair of the Rotator Cuff." The Journal of Bone and Joint Surgery, vol. 79-B, No. 3 (May 1997), pp. 458-461.

Burkhart, S.S., et al., "Cyclic Loading of Anchor-Based Rotator Cuff Repairs: Confirmation of the Tension Overload Phenomenon and Comparison of Suture Anchor Fixation with Transosseous Fixation." Arthoscopy: The Journal of Arthroscopic and Related Surgery, vol. 13, No. 6 (Dec. 1997), pp. 720-724.

Reed, S.C., et al., "Full-Thickness Rotator Cuff Repairs—A Biomechanical Comparison of Suture Versus Bone Anchor Techniques." The American Journal of Sports Medicine, vol. 24, No. 1, (1996), pp. 46-48.

Barber, F.A. et al., "Suture Anchor Strength Revisited." Arthroscopy: The Journal of Arthroscopic and Related Surgery, vol. 12, No. 1, (Feb. 1996), pp. 32-38.

Barber, F.A., et al., "Internal Fixation Strength of Suture Anchors—Update 1997." Arthroscopy: The Journal of Arthroscopic and Related Surgery, vol. 13, No. 3, (Jun. 1997), pp. 355-362.

Barber, F.A., et al., "Suture Anchors—Update 1999." Arthroscopy: The Journal of Arthroscopic and Related Surgery, vol. 15, No. 7, (Oct. 1999), pp. 719-725.

Gerber, C., et al., "Mechanical Strength of Repairs of the Rotator Cuff." The Journal of Bone and Joint Surgery, vol. 76-B, No. 3, (May 1994), pp. 371-380.

Gerber, C., "Experimental Rotator Cuff Repair." The Journal of Bone and Joint Surgery, vol. 81-A, No. 9, (Sep. 1999), pp. 1281-1290.

Goradia, V.K. et al., "Cyclic Loading of Rotator Cuff Repairs: A comparison of Bioabsorbable Tracks with Metal Suture Anchors and Transosseous Sutures." Arthroscopy: The Journal of Arthroscopic and Related Surgery, vol. 17, No. 4, (Apr. 2001), pp. 360-364.

France, E.P., "Biomechanical Evaluation of Rotator Cuff Fixation Methods." The American Journal of Sports Medicine, vol. 17, No. 2, (1989), pp. 176-181.

Vermeiren, J., et al. "Screw Fixation of a Complete Rotator Cuff Tear." Acta Orthopaedica Belgica, vol. 58, No. 1, (1992), pp. 88-90.

Robertson, D.B., et al., "Soft Tissue Fixation to Bone." The American Journal of Sports Medicine, vol. 14, No. 5, (1986), pp. 398-403.

Straight, C.B., et al.,."Soft Tissue Fixation to Bone-A Biomechanical Analysis of Spiked Washers." The American Journal of Sports Medicine, vol. 22, No. 3, (1994), pp. 393-343.

Magen, H.E., et al., "Structural Properties of Six Tibial Fixation methods for Anterior Cruciate Ligament Soft Tissue Grafts." The American Journal of Sports Medicine, vol. 27, No. 1, (1999), pp. 35-43.

Burkhart, S.S., et al., "Tissue Fixation Security in Transosseous Rotator Cuff Repairs: A Mechanical Comparison of Simple Cersus Matress Sutures." Arthroscopy: The Journal of Arthroscopic and Related Surgery, vol. 12, No. 6, (Dec. 1996), pp. 704-708.

Burkhart, S.S., et al., "The Rotator Crescent and Rotator Cable: An Anatomic Description of the Shoulder's Suspension Bridge." Arthroscopy: The Journal of Arthroscopic and Related Surgery, vol. 9, No. 6, (1996), pp. 611-616.

McLaughlin, H.L., "Lesions of the Musculotendinous Cuff on the Shoulder—The Exposure and Treatment of Tears with Retraction." Clinical Orthopaedics and Related Research, No. 304, (1994), pp. 3-9.

* cited by examiner

METHOD FOR USE IN REPAIRS OF INJURED SOFT TISSUE

CROSS-REFERENCE TO RELATED APPLICATIONS

This is a divisional of U.S. application Ser. No. 10/358,616, filed 5 Feb. 2003, entitled "System and Method for Use in Repairs of Injured Soft Tissue," which is incorporated herein by reference and to which priority is claimed.

BACKGROUND OF THE INVENTION

1. Field of the Invention

The present invention relates to an apparatus and method for repairing torn or avulsed soft tissue. More particularly, the present invention relates to an apparatus and method for providing a connection between healthy bone or soft tissue and selected other healthy bone or soft tissue to accommodate a stable, secure attachment that selectively immobilizes or minimizes movement of intervening injured soft tissue so that the soft tissue may properly heal.

2. Description of Related Art

A relatively common type of injury, especially in connection with sports, is injury in which soft tissue is torn or avulsed from the bone. This type of injury occurs in connection with many types of orthopedic injuries, such as torn or ruptured tendons and/or ligaments. In the shoulder, this type of injury often takes the form of a torn rotator cuff in which a portion of the rotator cuff tendons tear within themselves or avulse from their insertion into the bone. The present invention has been designed primarily for use in repair of torn rotator cuffs, and the description and discussion below will therefore focus on repair of rotator cuffs and the application of the invention to make such repairs. It will be apparent to those of ordinary skill in the art, however, in view of the following discussion and disclosure, that the present invention may be used for selected other orthopedic applications having similar parameters.

FIGS. 1 and 2 are views of a shoulder with typical torn rotator cuffs. In particular, FIGS. 1 and 2 are superior views of a shoulder with a tear associated with the supraspinatus muscle as it inserts into the humerus. The subscapularis muscle and the coracoid process are also shown in FIG. 1 for reference. The tear 1 shown in FIG. 1 is a simple tear, in which the tear 1 is generally perpendicular to the line of action of the muscle.

In FIG. 2, the tear 1 is more complex than the tear 1 in FIG. 1 because the injury in FIG. 2 has one or more branches 2 of the tear 1 parallel to the line of action of the muscle fibers, in addition to the main tear 1, which is substantially normal to the line of action of the muscle fibers.

In general, a torn rotator cuff, such as those shown in FIGS. 1 and 2, can lead to pain, weakness and loss of function. In many cases, the rotator cuff is repaired by surgically reconnecting the edges of the torn muscle or tendon. Repairs may also include reconnecting the edges of any interstitial tear in the tendons, as well as approximating or reattaching the torn edge of the soft tissue to the bone where it originated. As will be discussed in greater detail below, it is believed that the more common current and previous methods of repairing tears to soft tissue and the avulsion of soft tissue from bone include, but are not limited to, sutures, tacks or screws with spiked washers and staples.

Suture fixation of the tendon is believed to be the most common and classic method for approximating soft tissue to bone, and is generally accomplished by one of two different methods. In the first method, the sutures are typically passed through drill holes in the tuberosities and tied over a cortical bone bridge. In the second method, a suture anchor is typically employed where a device is fixed into a blind bone tunnel. Typically, the suture anchor has a suture eyelet on its trailing end, which provides for passage of suture through it. Recent studies have shown that on the bone side of the repair, suture anchor fixation is equal to or stronger than that of bone tunnels.

In both methods, the soft tissue side may be repaired by proper suture fixation. The torn free edge of the tendon, however, can be poor quality tissue if it is subjected to the degenerative process that is commonly involved in these tears. Some studies have shown that the soft tissue side of the repair when utilizing suture anchors can be the weakest link of the overall repair. A common mode of failure on the soft side of the repair is the result of suture pullout or the pulling of sutures through the muscle or tendon.

In order to lessen the risk of failure from pullout of the sutures from the soft tissue, several studies have been done testing various suture techniques and configurations. The so-called simple suture in which a single pass of the suture is made through the soft tissue is often believed to be the weakest configuration. This is commonly used, however, for arthroscopic repair of a tear because of its simplicity. Other more complicated techniques, such as the modified Mason-Allen stitch generally known to those skilled in the art, call for weaving the suture back and forth in the tissue, accessing the more normal tissue proximal to the tear. While this is a stronger construct, there is a concern of strangulating the tissue with multiple weaves, resulting in necrosis of the tendon. Also, this technique does not lend itself to arthroscopic repair of the tear.

Other methods used to combat the problem of suture tearing through tendon include soft tissue buttons (described in U.S. Pat. Nos. 5,306,290, 5,951,590, 6,074,409, and the "Tissue Button" by Arthrex), plates (such as described in U.S. Pat. No. 6,093,201) or washers (such as described in U.S. Pat. Nos. D0,404,128 and 6,206,886) that increase the effective surface area of the suture contact with the soft tissue and also aid in pressing the soft tissue against the bone at the repair interface. This tendon augmentation has been shown to resist failure perpendicular to the tendon fibers but may not reduce tendon shear parallel to the fibers, which is the failure mode when sutures tear through tendon.

Several other devices and techniques offer an alternative to suture fixation. These include screws, screws with spiked washers, tacks, and staples. Screw and tack fixation has been shown to allow adequate fixation of tendon to bone. The soft tissue side of the repair is addressed by using either a broad flat head as part of the screw as in the "Headed Bio-Corkscrew" by Arthrex, or using a separate spiked washer to engage the soft tissue as in the "Biocuff" by Bionix. Tacks such as the smooth and spiked "Suretac" by Acufex address the soft tissue side identically. Examples of devices in these categories are described in U.S. Pat. Nos. 5,013,316; 5,380,334; 5,601,558; 5,370,661; 6,096,060; 5,167,665; 5,893,856; and 5,013,316. Spiked washer technology (as described in U.S. Pat. Nos. 4,988,351; D0,374,287; D0,374,286; D0,368,777) with screw fixation to bone has a long history in other applications such as knee ligament reconstruction and conceivably offers some advantage in resisting pullout of the screw shank through those tendon fibers parallel to the direction of pull of the tendon. All of these methods are imperfect in that the point of fixation of the soft tissue is generally at the free torn edge, which, as noted above, can be of poor quality.

Security of tissue fixation is arguably the most important element in rotator cuff repair. The soft tissue side of the repair has been shown to be the weak link in the overall repair construct utilizing modern techniques. Current methods of obtaining fixation on the soft tissue side of the rotator cuff repair site appear to be limited in their effectiveness by several factors. The free torn edge of the tendon is relatively poor in quality as it is involved in the degenerative process leading to the tear. Arthroscopically placed simple sutures and all the non-suture devices discussed above gain fixation at this free torn edge. More complicated weaving sutures can overcome this problem by accessing more proximal tissue, which is healthier, thicker and stronger, but, as noted above, this may be at the expense of tissue necrosis and certainly does not lend itself to arthroscopic techniques. An additional concern is the range of motion through which a muscle is expected to function.

FIGS. 3A and 3B are superior views of a shoulder during internal and external rotations. From these figures it may be appreciated that soft tissues may experience wide ranges of motion and therefore may undergo dramatic variations in stresses. In addition to internal and external rotation, the shoulder may be moved through adduction and abduction motions (not shown), creating a wide variation in possible stresses at a particular point. It will be appreciated by those of ordinary skill in the art that a surgical repair of injured soft tissue, such as the tears shown in FIGS. 1 and 2, may require more complex repair methods and systems because of the different requirements at various points along the injured site. It would therefore be desirable to have a device adaptable to varying muscle requirements, and configurable to different attachment points or parts of the body being repaired. Accordingly, in order to overcome the apparent shortcomings of the currently available devices, a device is needed that securely fixes the soft tissue to the bone or other healthy soft tissue while augmenting the initial soft tissue side of the connection.

SUMMARY OF THE INVENTION

The present invention overcomes the disadvantages discussed above by providing an apparatus for use in repairing injured soft tissue in human beings, comprising a bridging member having a selected length adapted to provide a connection between a first point of attachment to healthy tissue or bone on a first side of a soft tissue injury and a second point of attachment to similarly healthy tissue or bone on an opposing, second side of such a soft tissue injury. The bridging member thereby provides a means to span the injured or degenerated tissue to provide secure connections to healthy attachment points that will hold the injured soft tissue in place and allow healing.

More particularly, the present invention provides a bridge member having a selected length adapted to provide connection between a first point of attachment on a first side of a soft tissue injury and a second point of attachment on the opposing side of such a soft tissue injury. The bridge member has a first connector end adapted for accommodating connection between the bridge member and a selected part of the body such as a bone or healthy soft tissue. The bridge member further comprises a second connector end adapted for accommodating connection between the bridge member and a second selected part of the body such as bone or healthy, soft tissue.

In a preferred aspect of the present invention, the first connector end of the bridge member is adapted for attachment to bone or soft tissue by means of suture tunnels or a suture anchor. In these embodiments, the bridging member is attached at the first connector end to the bone or healthy soft tissue and has a length selected to extend from the attachment point to other bone or healthy soft tissue.

In a more preferred alternative of this aspect of the invention, the second connector end includes an aperture sized and adapted to receive a soft tissue cleat such as is described in my co-pending patent application, U.S. patent application Ser. No. 09/963,132, which is hereby incorporated herein by reference for all purposes. The second end of the bridge member may then be attached to healthy soft tissue by means of the soft tissue cleat to provide a stable attachment between the two attachment points that will substantially immobilize the injured soft tissue to permit healing and repair.

In an alternative aspect of the present invention, the bridge member is comprised of a material and is shaped so that the bridge member is substantially rigid once it is fixed between the two attachment points. In this alternative embodiment, the bridge member acts to substantially immobilize the intervening soft tissue for repair.

In another alternative embodiment of the present invention, the bridge member is adapted for lateral and torsional flexing of the bridge member once it is secured between the bone and the soft tissue. In this embodiment, the bridge member does not permit movement along the longitudinal axis of the bridge member and only permits moderate movement in response to torsional or lateral flexing of the bridge member with movement of the healthy soft tissue to which it is attached.

In another alternative embodiment of the present invention, the bridge member is adapted for selected, elastic longitudinal stretching of the bridge member after attachment. The ability for the bridge member to change length, thereby changing the stress on the injured soft tissue, may promote blood flow, increase range of motion, and minimize atrophy.

In yet further alternative embodiments of the present invention, each of the connector ends may be adapted or modified to accommodate other means of connection between an anchor member and the body, that are known to those of ordinary skill in the art or will be known to those of skill in the art in view of the present disclosure. That is, the bridge member may be adapted to accommodate use of buttons, plates, screws, etc. in order to provide attachment between two healthy parts of the body and avoid attachment to degenerative or injured soft tissue.

Accordingly, the present invention overcomes the previously discussed problems by providing a means for obtaining a secure, stable attachment from healthy bone tissue or healthy soft tissue to other healthy soft tissue, thereby minimizing the possibility or likelihood of harm to damaged soft tissue that is the subject of repair. This and other advantages of the present invention will be further illustrated by the following description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

It is to be noted, however, that the appended drawings illustrate only exemplary embodiments of the invention and are therefore not to be considered limiting of its scope, for the invention may admit to other equally effective embodiments. In addition, although the figures may depict embodiments wherein the components represent different devices or loca

DETAILED DESCRIPTION OF THE INVENTION

The present invention overcomes the shortcomings of current soft tissue repair techniques by incorporating one or more bridge members of selected length to accommodate proper attachment across injured tissue in connection with the repair of such tissue. For illustrative purposes of this document, embodiments of the present invention and methods for using embodiments of the present invention are described as it may be used to repair rotator cuff tears. Those skilled in the art will recognize that the present invention is capable of repair of other soft tissue injuries without departing from the spirit or scope of the present invention.

Figure 4:
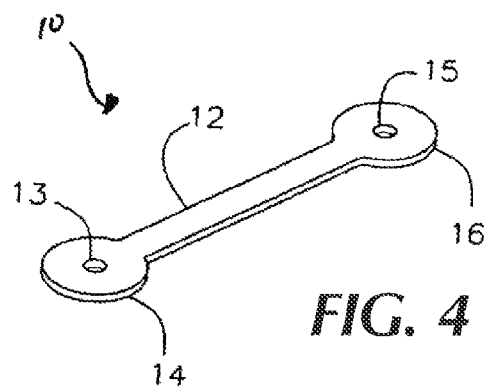
FIG. 4 is an isometric view of one embodiment of a bridge member.

Referring to FIG. 4, the present invention generally comprises a bridge member 10 that includes a bridging section 12 to which is attached a first connector end 14 and a second connector end 16. The bridging section 12 is adapted with a selected length adequate to span the injured tissue and to provide attachment to healthy attachment points. The bridging section 12 may be comprised of any of a number of materials that are appropriate for use in the human body and provide the desired flexibility, elasticity or rigidity for a particular application. Examples of materials that may be used to construct the bridging section 12 include, but are not limited to, polyethylene, an orthopedic plastic manufactured under the trade name DELRIN, bioabsorbable materials, and biologic materials, and/or combinations of these materials. Ideally, the bridging section 12 has a cross section adapted for non-injurious contact with the injured tissue to minimize the possibility of cutting or otherwise further injuring the tissue, and furthermore having a minimal thickness to reduce the volume of the device when in place in the body. The particular thickness and width in cross-sectional shape of the bridging section 12 may be varied with the material that is used to construct the bridging member 10 in order to provide the requisite strength for a given application. It is believed that this element of design will be known to those of ordinary skill in the art in light of the present disclosure.

In designing the bridging section 12, different degrees of flexibility or elasticity may be desirable. For example, in some repair situations, it may be beneficial for the bridge member 10 to be substantially rigid. In other situations, it may be beneficial for healing if the bridge member 10 has some degree of flexibility, such as lateral or torsional flexibility. Further, in some situations, it may be beneficial for the bridge member 10 to have some degree of elasticity, so that a selected degree of the stretching of the bridge member 10 longitudinally is permitted. Such flexibility or elasticity may be desirable to permit limited movement of the spanned tissue—both the injured tissue and the healthy tissue—to stimulate blood flow and to permit healing. Accordingly, it is contemplated under the present invention that the material of which the bridging section 12 is comprised will be selected to provide the desired degree of flexibility and/or elasticity for a particular application for a particular type of repair.

Referring still to FIG. 4, the bridge member 10 further includes a first connector end 14 attached to the bridging section 12. The first connector end 14 is adapted to accommodate attachment of the bridge member 10 to bone or healthy tissue. Therefore, first connector end 14 may take a number of suitable shapes providing appropriate apertures or attachment members to enable attachment of the bridge member 10 to the bone or healthy tissue. In the preferred embodiment, the first connector end 14 has a generally flat, circular shape as shown in FIG. 4 in order to provide sufficient material strength to support the connection between the bone and the healthy tissue and the bridging section 12. In the preferred embodiment, the first connector end 14 further has an aperture 13 adapted to receive an attaching device such as a suture or a mechanical fastener. As will be appreciated in light of the present disclosure, aperture 13 is sized and configured to be complementary with the anticipated attaching device for the particular application.

As with the bridging section 12, the first connector end 14 may be comprised of any of a number of materials suitable for use in human beings. For example, the first connector end 14 may be comprised of metal or orthopedic plastic. Because the first connector end 14 must accommodate the secure attachment of the bridge member 10 to healthy bone or tissue, in the preferred embodiment, the first connector end 14 will be substantially rigid or have only moderate flexibility in order to provide a stable attachment point with the bone or healthy tissue.

The first connector end 14 may be connected to the bridging section 12 in a number of ways suitable for providing a non-detachable connection between the first connector end 14 and the bridging section 12. In the preferred embodiment, it is contemplated that the bridge member 10 will be formed as a unitary body such that the bridging section 12, the first connector end 14, and the second connector end 16 are all integrally formed as a single piece.

Referring still to FIG. 4, the bridge member 10 also includes a second connector end 16 adapted to enable attachment of the bridge member 10 to a different, opposing section of healthy bone or tissue from the bone or tissue to which the first connector end 14 was secured. In the simplest preferred embodiment, the second connector end 16 has a shape and configuration similar to the first connector end 14 and includes an aperture 15 as shown in FIG. 4. In the simplest embodiment, the second connector end 16 is made of the same material that is similar to the material that is used to make the bridging section 12 and the first connector end 14 and, in a preferred aspect of this embodiment, is formed as part of a unitary body with the bridging section 12 and the first connector end 14.

As discussed above, the length of the bridging section 12 and of the bridge member 10 is selected to enable the device of the present invention to be attached at two healthy attachment points and span injured tissue. The necessary length and shape of the bridge member 10, therefore, will vary with the particular application and the extent of the injury to be repaired. Referring to FIGS. 5, 6, 7, and 8, there are shown alternative embodiments of the present invention that are designed to accommodate the repair of situations of differing lengths and shapes.

Figure 5:
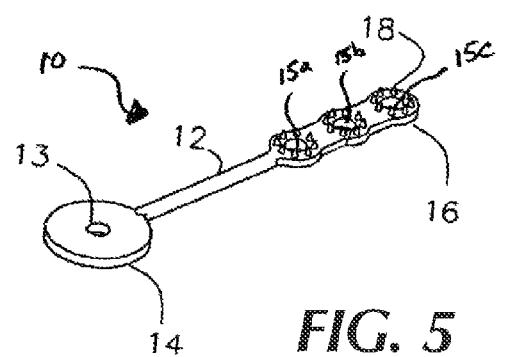
FIG. 5 is an isometric view of another embodiment of a bridge member.

For example, in the embodiment shown in FIG. 5, the bridge member 10 comprises an elongated second connector end 16 having a plurality of apertures designated as 15a, 15b, and 15c, selectively positioned along the length of the second connector end 16. In use, the bridge member 10 can be severed before the attachment aperture 15c or before the attachment aperture 15b depending upon the overall length that is needed for the bridge member 10.

Figure 6:
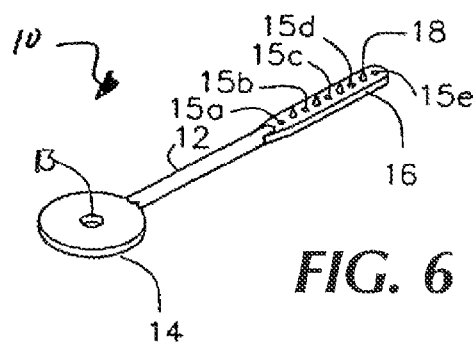
FIG. 6 is an isometric view of another embodiment of a bridge member.

Referring to FIG. 6, there is shown an alternative that is similar in nature to the embodiment shown in FIG. 5. In particular, the embodiment shown in FIG. 6 comprises a plurality of apertures 15a, 15b, 15c, 15d, and 15e, all disposed along the length of the second connector end 16 to accommodate the selective attachment of the bridge member 10 across soft tissue of a determined length.

Referring still to FIGS. 5 and 6, the bridge member 10 may further include surface fasteners 18 on any surface that is intended to contact soft tissue. The surface fasteners 18 may take the form of spikes, barbs, or other mechanical features that penetrate the soft tissue and/or enhance fixation at the bone/tendon interface. In FIGS. 5 and 6, the surface fasteners 18 are depicted by way of example as many spikes.

Referring still to FIGS. 4-8, the embodiments shown depict bridge member 10 having a first connector end 14 that is generally circular in shape and a second connector end 16 that varies in length. It is to be understood by those skilled in the art that the shapes and lengths of the attachment ends may be varied in selectively determining the length of the attachment member in accordance with the present invention. Just as the shape and length of the respective attachment ends 14 and 16 may be varied to provide greater flexibility in terms of length and use, the shape and configuration of the apertures 13 and 15 may also be varied to accommodate different means of fastening. For example, an end may be configured to have an aperture of suitable diameter and have additional selectively spaced apertures of smaller diameter to accommodate the use of a soft tissue cleat to attach the end to soft tissue. Similarly, the holes 13 or 15 may be varied in size to accommodate use of sutures, screws, or other attaching devices.

Figure 7:
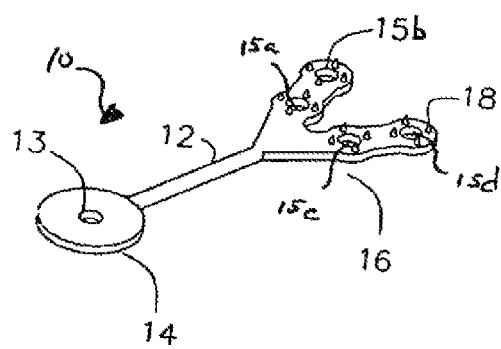
FIG. 7 is an isometric view of another embodiment of a bridge member.
Figure 8:
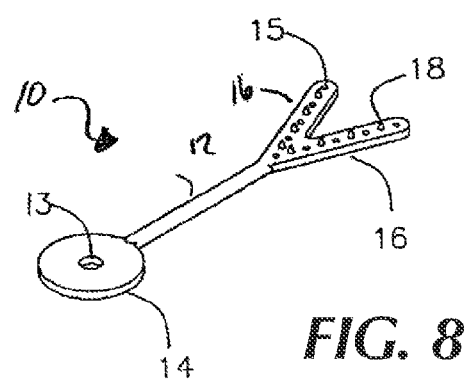
FIG. 8 is an isometric view of another embodiment of a bridge member.

Referring now to FIGS. 7 and 8, there are shown alternative embodiments having irregularly shaped or multiple attachment ends 16 to accommodate multiple points of fixation and to accommodate the spanning of more complex injury sites. It will be appreciated, based upon the present disclosure, that other geometric configurations could be utilized to provide differing numbers of extensions and differing lengths to address particular injuries.

Figure 9:
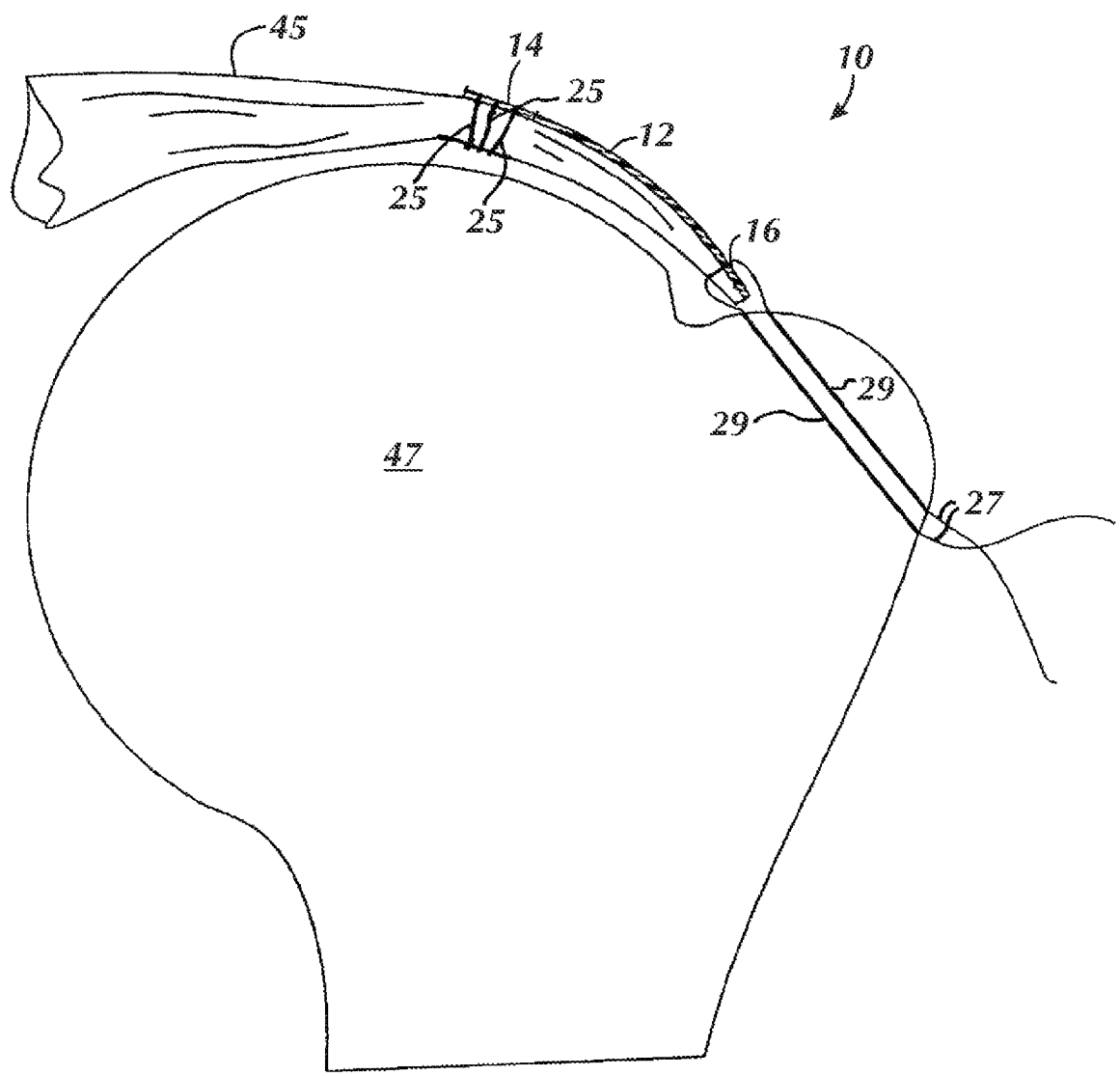
FIG. 9 is a cross-sectional view demonstrating the use of a bridge member according to one embodiment of the present invention in a repair of a rotator cuff tear utilizing suture fixation and bone tunnels.

FIG. 9 is a view of a shoulder soft tissue repair site illustrating use of a bridge member 10 in accordance with one embodiment of the present invention. In this example, the bridge member 10 attaches to healthy soft tissue 45 on the proximal side of the injury using sutures 25, spans the injured tissue, and reattaches the injured tissue to the healthy bone tissue 47 at a second point of attachment through the use of sutures 27 and bone tunnels 29.

In particular, the sutures 25 attach a first connector end 14 of the bridge member 10 to the healthy rotator cuff tissue 45 proximal to the torn edge of the injured tissue, where the tissue is thicker and stronger. Additionally, spikes 18 (not shown) on the undersurface of the bridge member 10 may be used to enhance fixation of the bridge member 10 to the soft healthy tissue 45.

Typically, in this repair, one or more tunnels 29 are drilled through bone tissue 47 at a second point of attachment. Suture 27 passes through one tunnel 29, through a portion of the rotator cuff soft tissue 45, through an opening or other feature in the bridge member 10 and through a second tunnel 29 in the bone 47. The suture 27 is tied over the outside of the bone 47 over a cortical bridge between the tunnels 29. The soft tissue 45 is thereby reattached to the bone 47 using a bridge member 10 to augment the soft tissue side of the repair.

Figure 10:
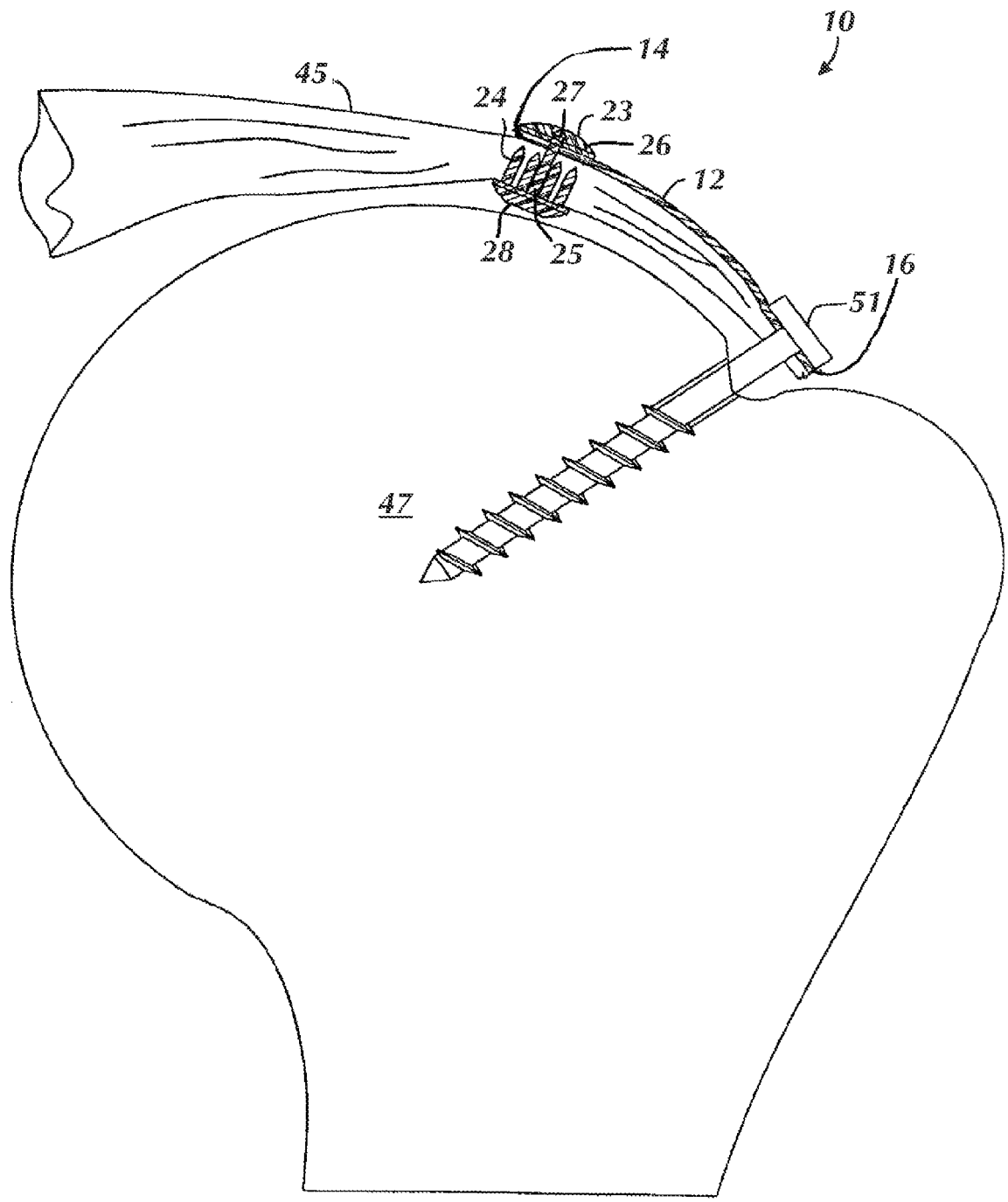
FIG. 10 is a cross-sectional view demonstrating the use of a bridge member according to one embodiment of the present invention in a repair of a rotator cuff tear utilizing a soft tissue cleat and a screw.

FIG. 10 is a view of another example of a shoulder soft tissue repair site in which rotator cuff tissue 45 is reconnected to healthy bone tissue 47 using a bridge member 10 in accordance with one embodiment of the present invention. In this example, reattachment of the avulsed tissue 45 is accomplished using a soft tissue cleat 23 to connect the bridge member 10 to a portion of healthy soft tissue 45, and screw 51 to connect to the bridge member 10 and reattach the avulsed tissue 45 to the bone tissue 47.

In particular, first connector end 14 of the bridge member 10 is of a design adapted to accommodate connection to a soft tissue cleat 23, such as described in co-pending U.S. patent application Ser. No. 09/963,132. In this embodiment, the soft tissue cleat 23 connects a first connector end 14 of a bridge member 10 to a healthy portion of the rotator cuff tissue 45 proximal to the torn edge, where the tissue is thicker and stronger. Spikes 24 on the soft tissue cleat 23 may be utilized to enhance fixation of the bridge member 10 to the healthy soft tissue 45.

As disclosed in co-pending U.S. patent application Ser. No. 09/963,132 and as shown in FIG. 10, the soft tissue cleat 23 is used for coapting soft tissue of the rotator cuff tissue 45 and the connection end 14 of the bridging member 10. The soft tissue cleat 23 includes a first disc or side 26 and a second disc or side 28. The first disc 26 is attached to the second disc 28 to coapt an area of soft tissue 45 at the connection end 14 of the bridging member 10. The first disc 26 has a plurality of fixed-length projections or spikes 24 and 25 extending perpendicularly from the bottom surface of the first disc 26. The projections or spikes 24 and 25 of the first disc 26 are configured to perforate the soft tissue 45. The second disc 28 has at least one indention 29 configured to receive a portion of at least one of the projections or spikes 25. This at least one spike 25 is positioned through the aperture 15 in the connection end 14 and is securely joined to the indentation 29 in the second disc 28. In one aspect of the present invention, the indention 29 in the second disc 28 has a mechanical locking mechanism for securely joining to the at least one spike 25 of the second disc 26.

The bridge member 10 spans the torn edge of the rotator cuff 45 to a portion of healthy bone tissue 47, where screw 51 is used to attach the second connector end 16 of bridge member 10 to the bone 47. In this embodiment, bridge member 10 is adapted to accommodate connection to screw 51 and operable to facilitate reattachment of avulsed soft tissue 45 to the bone 47.

Figure 11:
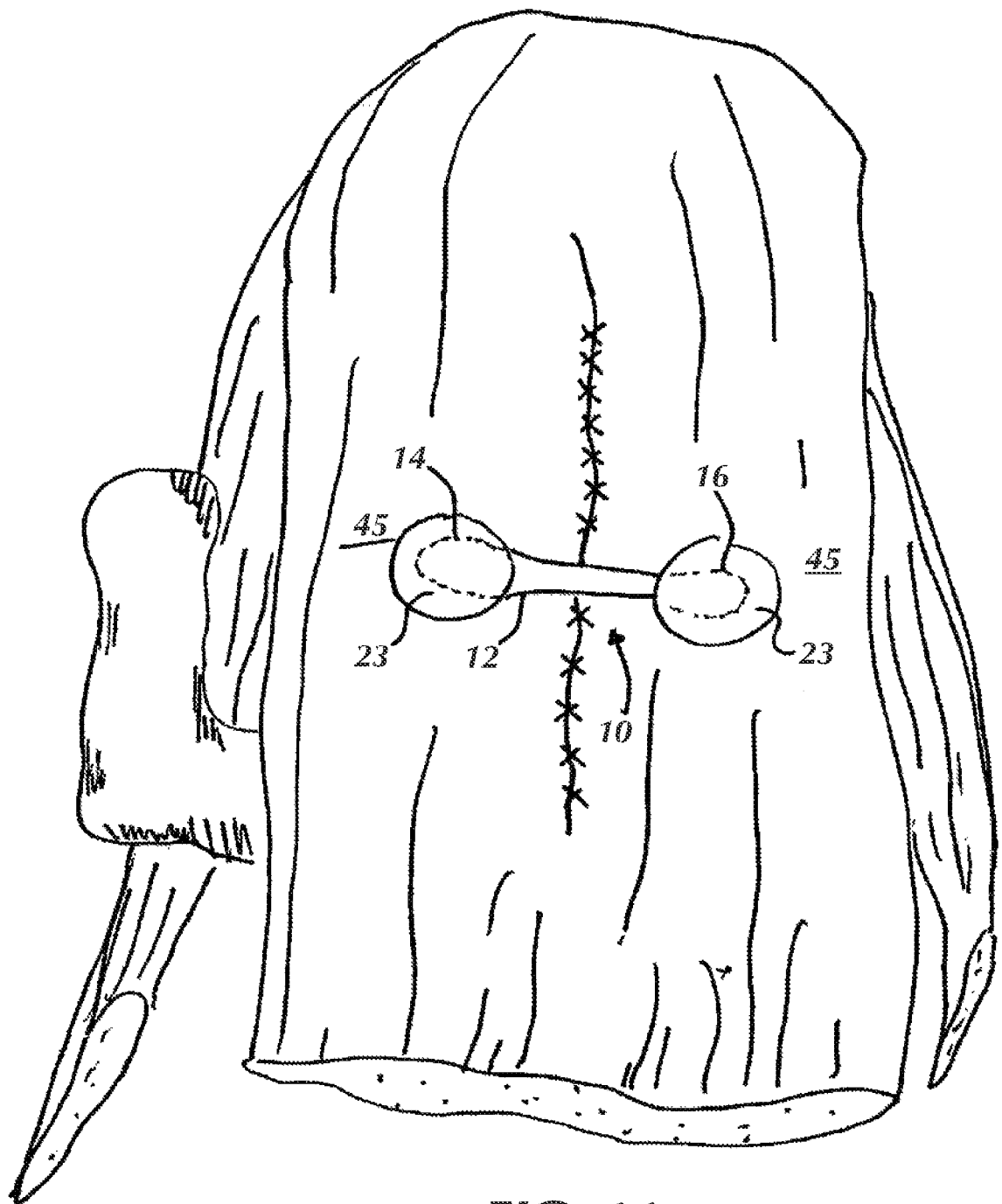
FIG. 11 is a cross-sectional view demonstrating the use of a bridge member according to one embodiment of the present invention in a repair of a rotator cuff tear utilizing soft tissue cleats.

FIG. 11 is a view of a soft tissue repair in which portions of soft tissue 45 are reconnected using tissue anchors, such as, but not limited to, soft tissue cleats as described in copending U.S. patent application Ser. No. 09/963,132, on both sides of the injury. In this embodiment, both first and second connector ends 14 and 16 are of a design adapted to accommodate connection to a soft tissue cleat 23, such as described in co-pending U.S. patent application Ser. No. 09/963,132.

The soft tissue cleat 23 connects the bridge member 10 to a healthy portion of the rotator cuff tissue 45 where the tissue 45 is thicker and stronger. Spikes (not shown) on the soft tissue cleat 23 and spikes (not shown) on the undersurface of the second connector end 16 of the bridge member 10 may be included to enhance fixation of the bridge member 10 to the healthy soft tissue 45. The bridge member 10 spans the torn portion of the rotator cuff to a second point of attachment on the opposite side of the injury site in another portion of healthy soft tissue 45. Reconnection of the portions of the soft tissue 45 is thereby accomplished with bridge member 10 and soft tissue cleats 23 to provide augmentation to the soft tissue repair.

Figure 12:
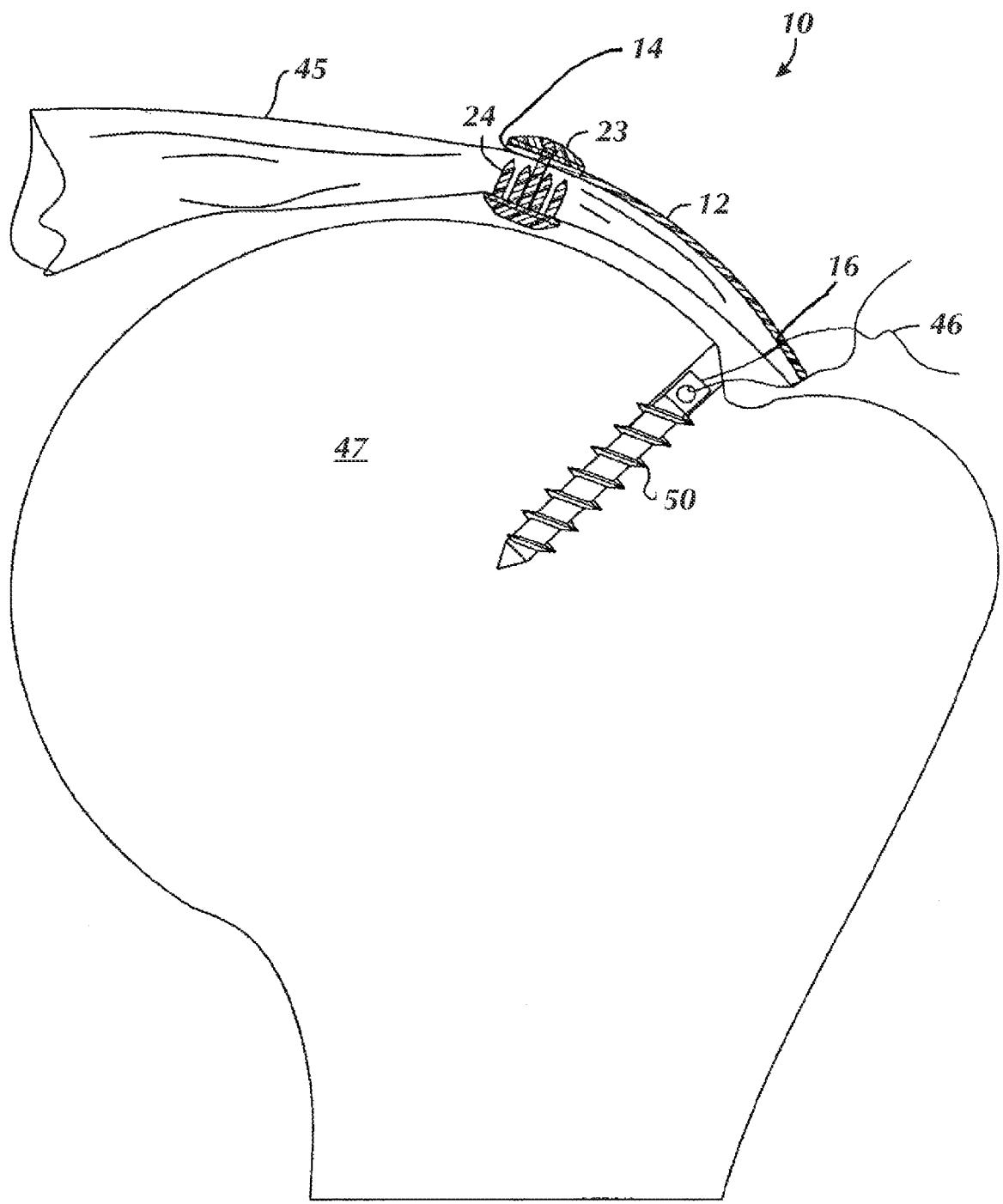
FIG. 12 is a cross-sectional view illustrating the use of a bridge member according to one embodiment of the present invention in a repair of a rotator cuff tear utilizing a suture anchor and a soft tissue cleat.

FIG. 12 is a cross-sectional view of a soft tissue repair site in which a bridge member 10 according to one embodiment of the present invention, a tissue anchor 23, and a suture anchor 50 are utilized in order to reattach an avulsed rotator cuff tissue to the proximal humerus 47.

In this example, a soft tissue cleat 23, such as described in co-pending U.S. patent application Ser. No. 09/963,132, securely attaches a first connector end 14 of the bridge member 10 to the healthy rotator cuff muscle 45 proximal to the torn edge of the injured tissue where the tissue is thicker and stronger. Spikes 24 on the soft tissue cleat 23 enhance fixation of the bridge member 10 to the healthy soft tissue 45.

The bridge member 10 spans the injury site and is adapted for connection to the bone tissue 47 by means of a suture anchor 50 and sutures 46. Typically, the suture anchor 50 is engaged into bone 47. The suture 46 passes through an aperture of suture anchor 50, through a selected portion of tissue 45 that has avulsed from the bone 47, and through an aperture 15 in the second connector end 16 of bridge member 10, such that the soft tissue 45 is affixed to the bone 47. In this manner, the soft tissue 45 is supported through the healing process with the bridge member 10 facilitating reattachment of the avulsed soft tissue 45 to the bone 47. The rotator cuff is thereby repaired using a bridge member 10 and soft tissue cleat 23 to augment the construct.

Advantageously, embodiments of the present invention may provide improved pullout strength due in part to a moment generated by the bridge member 10 in contact with a soft tissue cleat 23. In some embodiments, the moment is generated on the soft tissue cleat 23 when the muscle 45 contracts. The moment typically causes the soft tissue cleat 23 to tilt with respect to the line of action of the muscle pull, such that portions of the soft tissue cleat 23 are compressed into the soft tissue 45. The result of a tilted fastener is a larger surface area than that of any penetrating sutures, posts, or barbs, contacting the soft tissue to increase pullout strength. Therefore, a larger surface area of a soft tissue cleat 23, tilted at some angle, may be advantageous for enhancing the fixation and pullout strength of the soft tissue cleat 23. With the tilt, a central fixation peg or peripheral projections or both, and portions of the all contribute to the overall pullout strength of the repair. Without the tilt, the only surface areas resisting pullout are those of a central fixation peg or peripheral projections or both.

Figure 1:
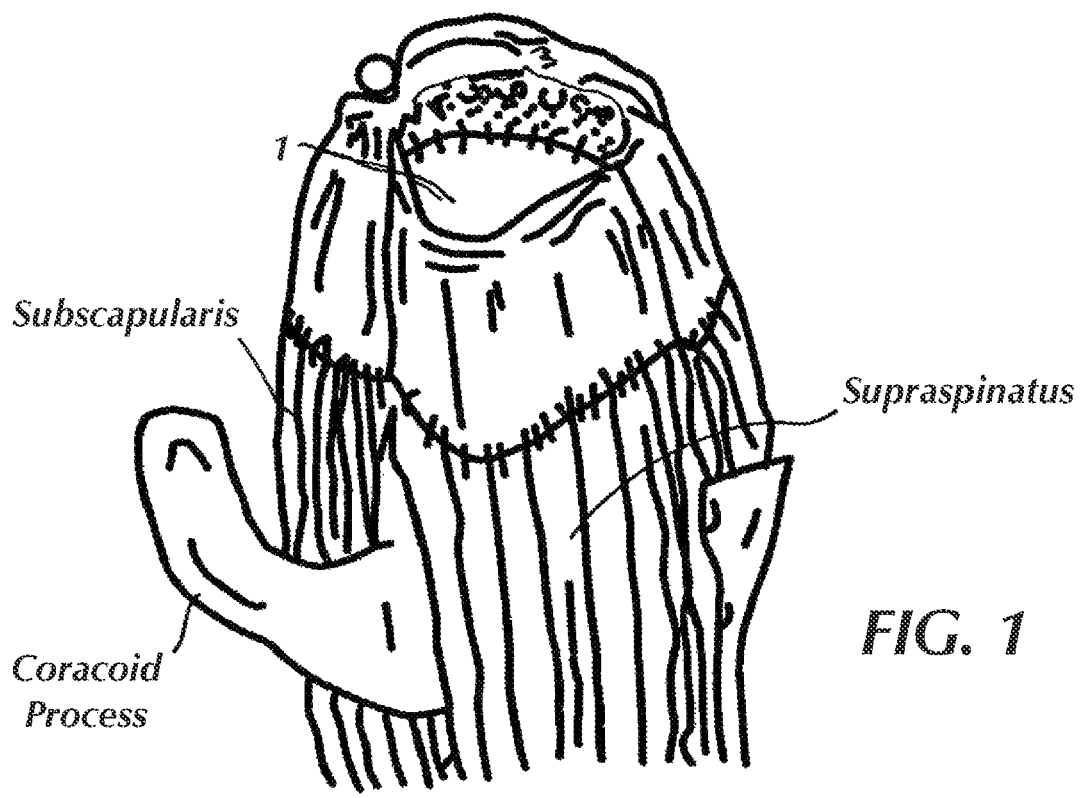
- FIG. 1 is a superior view of the shoulder and rotator cuff demonstrating a tear in the rotator cuff
Figure 13:
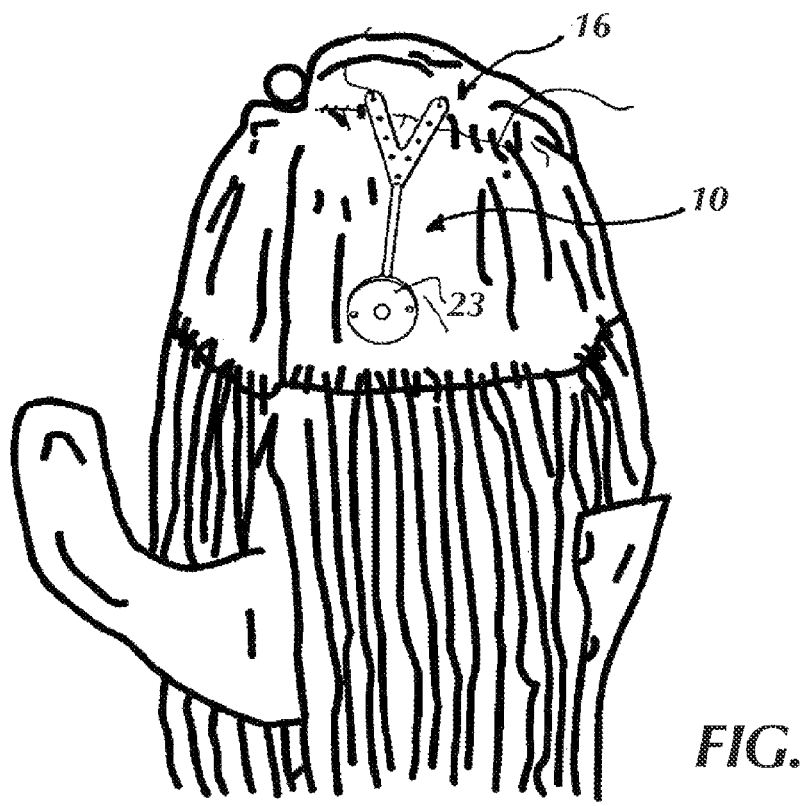
FIG. 13 is a superior view of the shoulder as shown in FIG. 1 with the torn rotator cuff repaired using interrupted sutures and augmented with an embodiment of the present invention.

FIG. 13 is a view of a shoulder with a tear in a rotator cuff similar to the tear illustrated in FIG. 1, repaired using a bridge member 10 according to one embodiment of the present invention similar to the system shown in FIG. 12. In addition to repairing the tear (accomplished here by a technique of interrupted sutures), the repair is augmented with a bridge member 10 similar to those shown in FIGS. 9 and 11, and a soft tissue cleat 23. Those of skill in the art will appreciate the improved stability and strength of the repaired injury augmented by a bridge member 10, which in this figure comprises a bifurcated second connector end 16 to distribute forces or to accommodate variations in stress occurring from motion of the shoulder.

Figure 2:
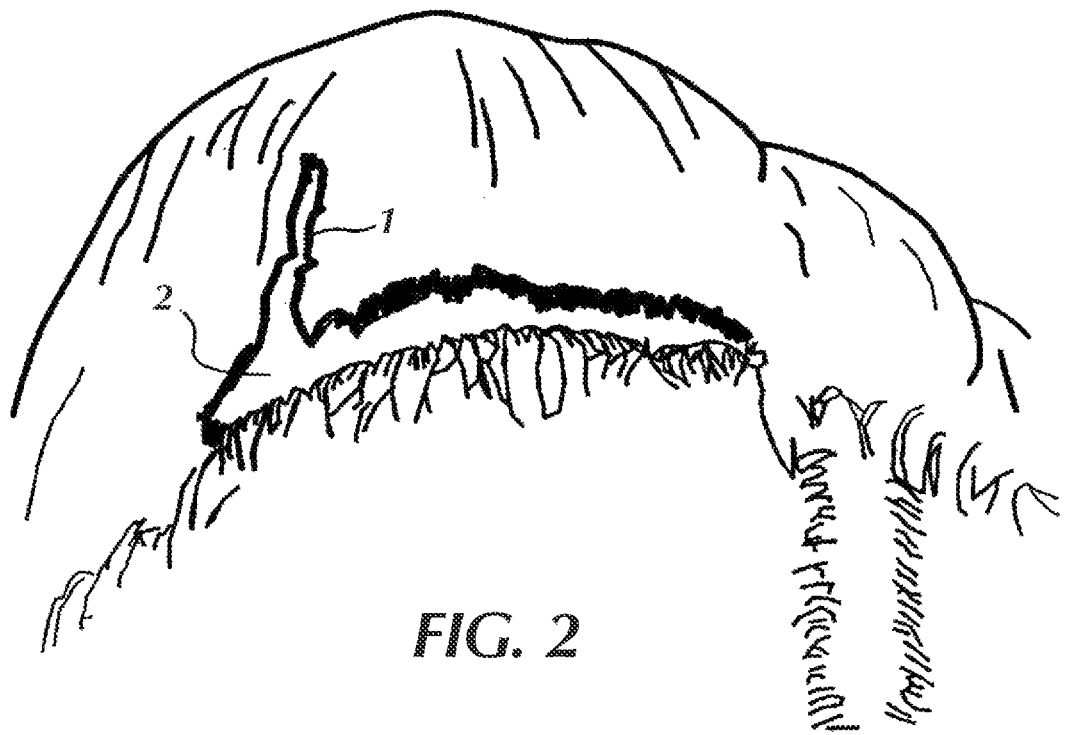
FIG. 2 is a superior view of the shoulder and rotator cuff demonstrating a tear in the rotator cuff.
Figure 3A:
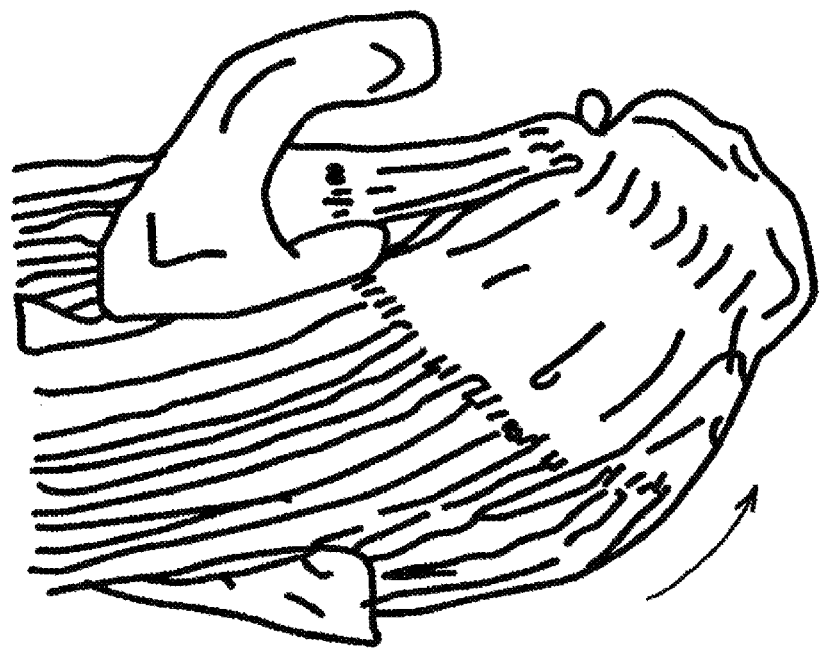
FIGS. 3A and 3B are superior views of the shoulder and rotator cuff in full internal rotation and full external rotation, respectively.
Figure 3B:
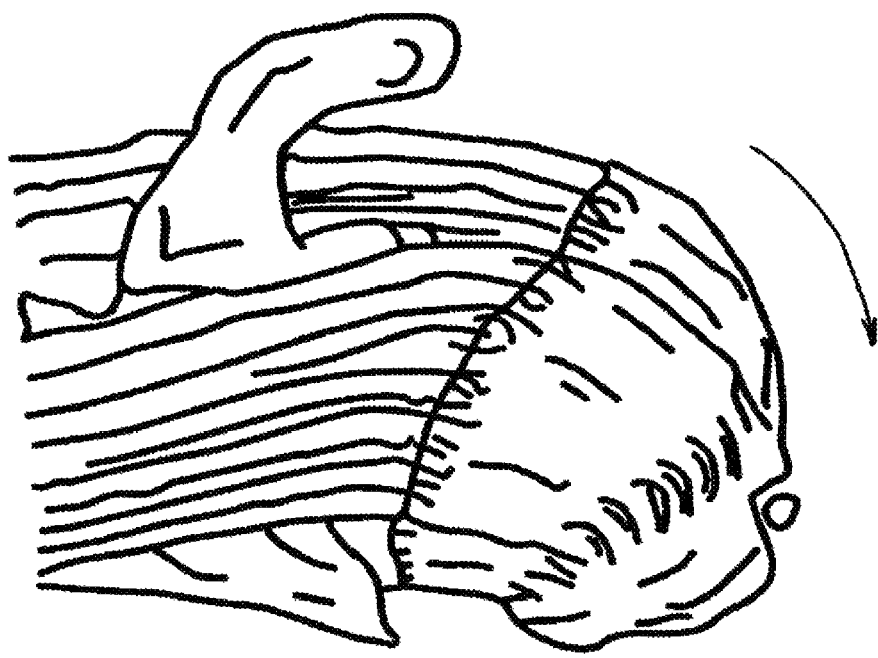
Figure 14:
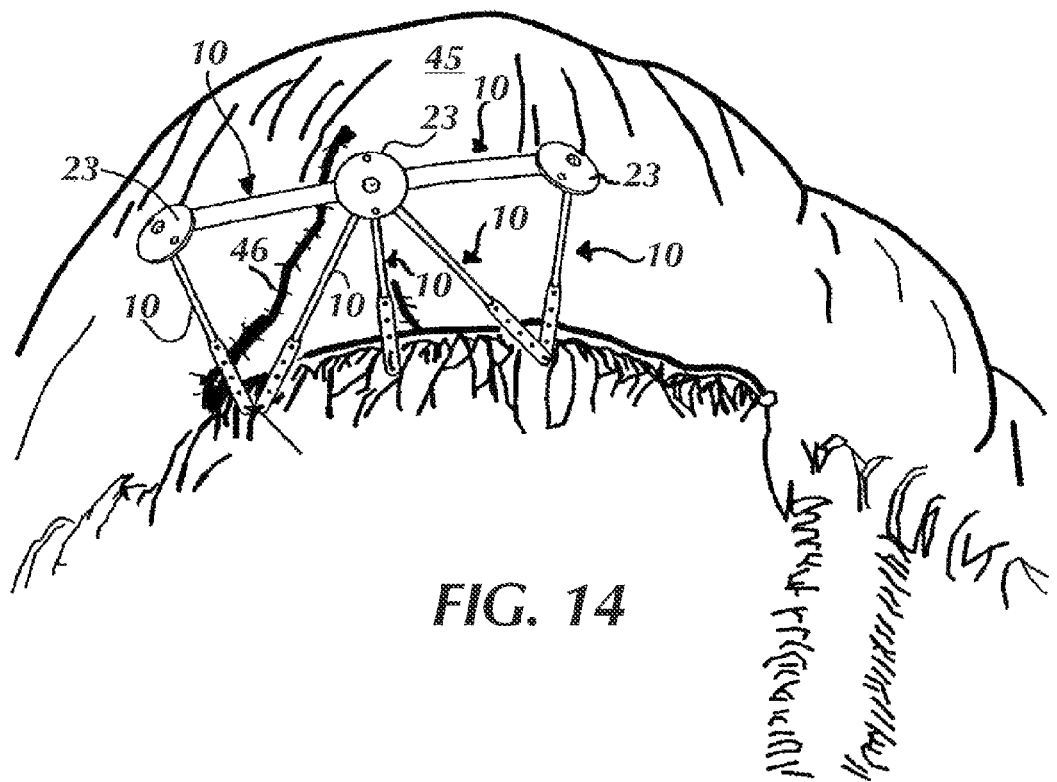
FIG. 14 is a superior view of the shoulder, as shown in FIG. 2 with the torn rotator cuff repaired using interrupted sutures and augmented with an embodiment of the present invention.

FIG. 14 is a view of an injured rotator cuff as shown in FIG. 2. In this case, the edges of the torn rotator cuff have been reconnected using interrupted sutures 46. In addition, the repair has been augmented utilizing a system of interconnected bridge members 10. In various aspects of this embodiment, bridge members 10 are connected at a single attachment point on one end and their other ends are spaced at different attachment points in healthy soft tissue 45 on the other side of the injury. Furthermore, bridge members 10 are connected to each other and connected to healthy soft tissue 45 on the same side of the injury, which may provide even more strength and stability to the repair. In this manner, the present invention may be used to emulate the structure or function of a trestle.

Advantageously, the use of a bridge member with current tissue anchors, sutures, and particularly soft tissue cleats may shorten the amount of time needed to perform a repair procedure. It will be obvious in view of the present disclosure and description that the present invention provides a secure connection for repairing soft tissue injuries, in a convenient form. Therefore, instead of the surgeon spending time suturing through soft tissue or connecting a suture to a tissue anchor on the bony side of the repair, the surgeon is able to focus on optimum placement for anchoring devices and connecting the ends to the appropriate anchoring device.

The present invention has been disclosed in connection with specific embodiments. However, it will be apparent to those of skill in the art that variations from the illustrated embodiments may be undertaken without departing from the spirit and scope of the present invention. For example, a soft tissue cleat, screw, or suture anchor may be incorporated into an attachment end. Additionally, embodiments of the present invention may be attached to attachment points not located in healthy soft tissue. Furthermore, the present invention may be adapted to accommodate connection to other mechanical fasteners such as staples or tacks to facilitate secure connections. These and other variations will be apparent to those skilled in the art in view of the above disclosure and are within the spirit and scope of the invention.

As used in this specification and in the appended claims, it should be understood that the word "a" does not preclude the presence of a plurality of elements accomplishing the same function.

What is claimed is:

1. A soft tissue surgical repair method comprising the steps of:
attaching a first end of a first bridge member on one side of a soft tissue injury by coapting the first end to soft tissue with mating members of a cleat, and
coapting one or more ends of one or more additional bridge members to the soft tissue along with the first end using the same mating members of the cleat;
attaching a second end of the first bridge member to bone tissue using a fastener; and
using a bridging section between the first and second ends to support forces associated with the intervening soft tissue.

2. The method of claim 1, wherein coapting the first end to the soft tissue with the mating members of the cleat comprises:
positioning the first end against one surface of the soft tissue;
passing at least one spike of one of the mating members through an aperture in the first end;
perforating the soft tissue with the at least one spike; and
connecting the at least one spike to another of the mating members on an opposing surface of the soft tissue.

3. The method of claim 1, wherein the fastener comprises a screw, and wherein the method comprises:
positioning the screw through an aperture in the second end;
positioning the screw through soft tissue; and
screwing the screw into the bone tissue to coapt the soft tissue between the second end and the bone tissue.

4. The method of claim 1, wherein the fastener comprises a suture anchor, and wherein the method comprises:
screwing the suture anchor into the bone tissue; and
suturing the second end of the bridge member along with soft tissue to the suture anchor.

5. The method of claim 1, wherein the fastener comprises suture, and wherein the method comprises:
creating a bone tunnel in the bone tissue; and
suturing the second end of the bridge member along with soft tissue to the bone tissue through the bone tunnel.

6. A soft tissue surgical repair method comprising the steps of:
attaching a first end of a first bridge member on one side of a soft tissue injury by
coapting the first end to soft tissue with mating members of a first cleat, and
coapting one or more ends of one or more additional bridge members to the soft tissue along with the first end using the same mating members of the first cleat;
attaching a second end of the first bridge member on another side of the soft tissue injury; and
using a bridging section between the first and second ends to support forces associated with the intervening soft tissue between the sides of the soft tissue injury.

7. The method of claim 6, wherein coapting the first end to the soft tissue with the mating members of the first cleat comprises:
positioning the first end against one surface of the soft tissue;
passing at least one spike of one of the mating members through an aperture in the first end;
perforating the soft tissue with the at least one spike; and
connecting the at least one spike to another of the mating members on an opposing surface of the soft tissue.

8. The method of claim 6, wherein attaching the second end comprises coapting the second end to soft tissue with mating members of a second cleat.

9. The method of claim 8, wherein coapting the second end to the soft tissue with the mating members of the second cleat comprises:
positioning the second end against one surface of the soft tissue;
passing at least one spike of one of the mating members through an aperture in the second end;
perforating the soft tissue with the at least one spike; and
connecting the at least one spike to another of the mating members on an opposing surface of the soft tissue.

10. The method of claim 6, wherein attaching the second end comprises suturing the second end to soft tissue.

11. The method of claim 10, wherein suturing the second end comprises passing suture through one or more of a plurality of apertures on the second end of the first bridge member.

12. The method of claim 10, wherein the second end of the first bridge member comprises at least two split portions, each split portion having a plurality of apertures, and wherein suturing the second end comprises passing suture through one or more of the apertures on the at least two split portions.

13. The method of claim 6, wherein the method comprises building an interconnected network of the first and additional bridge members across the soft tissue injury by coapting the first ends of the first and additional bridge members to soft tissue on the one side using the mating members of the first cleat and additional cleats and attaching at least some of the second ends of the first and additional bridge members to soft tissue on the other side of the soft tissue injury.

14. A soft tissue surgical repair method comprising the steps of:
attaching a first end of a first bridge member on one side of a soft tissue injury by coapting the first end to soft tissue with mating members of a first cleat;
attaching a second end of the first bridge member on another side of the soft tissue injury by coapting the second end to soft tissue with mating members of a second cleat; and
using a bridging section between the first and second ends to support forces associated with the intervening soft tissue.

15. The method of claim 14, wherein attaching the second end of the first bridge member on the other side of the soft tissue injury comprises attaching the second end along with soft tissue to bone tissue.

16. The method of claim 14, wherein coapting the first end to soft tissue with mating members of a first cleat comprises:
positioning the first end against one surface of the soft tissue;
passing at least one spike of one of the mating members of the first cleat through an aperture in the first end;
perforating the soft tissue with the at least one spike; and
connecting the at least one spike to another of the mating members of the first cleat on an opposing surface of the soft tissue.

17. The method of claim 14, wherein coapting the second end to soft tissue with mating members of a second cleat comprises:
positioning the second end against one surface of the soft tissue;
passing at least one spike of one of the mating members of the second cleat through an aperture in the second end;
perforating the soft tissue with the at least one spike; and
connecting the at least one spike to another of the mating members of the second cleat on an opposing surface of the soft tissue.

18. The method of claim 14, wherein the method comprises building an interconnected network of the first and one or more additional bridge members across the soft tissue injury by coapting the first ends of the first and one or more additional bridge members to soft tissue on the one side using the mating members of the first cleat and the first cleat and one or more additional cleats and attaching the second ends of the first and one or more additional bridge members to soft tissue on the other side of the soft tissue injury.

19. A soft tissue surgical repair method comprising the steps of:
attaching a first end of a first bridge member on one side of a soft tissue injury by coapting the first end to soft tissue with mating members of a first cleat;
attaching a second end of the first bridge member on another side of the soft tissue injury by suturing the second end to soft tissue, wherein the second end of the first bridge member comprises at least two spit portions, each split portion having a plurality of apertures, and wherein suturing the second end comprises passing suture through one or more of the apertures on the at least two split portions; and
using a bridging section between the first and second ends to support forces associated with the intervening soft tissue between the sides of the soft tissue injury.

20. The method of claim 19, wherein coapting the first end to the soft tissue with the mating members of the first cleat comprises:
positioning the first end against one surface of the soft tissue;
passing at least one spike of one of the mating members through an aperture in the first end;
perforating the soft tissue with the at least one spike; and
connecting the at least one spike to another of the mating members on an opposing surface of the soft tissue.

21. The method of claim 19, wherein attaching the second end of the first bridge member on the other side of the soft tissue injury comprises attaching the second end along with soft tissue to bone tissue.

22. The method of claim 19 wherein the method comprises building an interconnected network of the first and one or more additional bridge members across the soft tissue injury by coapting the first ends of the first and one or more additional bridge members to soft tissue on the one side using the mating members of the first cleat and the first cleat and one or more additional cleats and attaching the second ends of the first and one or more additional bridge members to soft tissue on the other side of the soft tissue injury.

23. A soft tissue surgical repair method comprising the steps of:
building an interconnected network of bridge members across a soft tissue injury;
attaching first ends of the interconnected bridge members on one side of the soft tissue injury by coapting the first ends to soft tissue with mating members of one or more cleats;
attaching second ends of the interconnected bridge members on another side of the soft tissue injury; and
using bridging sections between the first and second ends to support forces associated with the intervening soft tissue between the sides of the soft tissue injury.

24. The method of claim 23, wherein coapting the first ends to the soft tissue with the mating members of the one or more cleats comprises:
positioning the first end against one surface of the soft tissue;
passing at least one spike of one of the mating members through an aperture in the first end;
perforating the soft tissue with the at least one spike; and
connecting the at least one spike to another of the mating members on an opposing surface of the soft tissue.

25. The method of claim 23, wherein attaching the second ends comprises suturing one or more of the second ends to soft tissue.

26. The method of claim 23, wherein attaching the second ends comprises coapting one or more the additional end to soft tissue with mating members of one of more second cleats.

27. The method of claim 23, wherein attaching the second ends comprises attaching one or more of the second ends along with soft tissue to bone tissue.

* * * * *